United States Patent

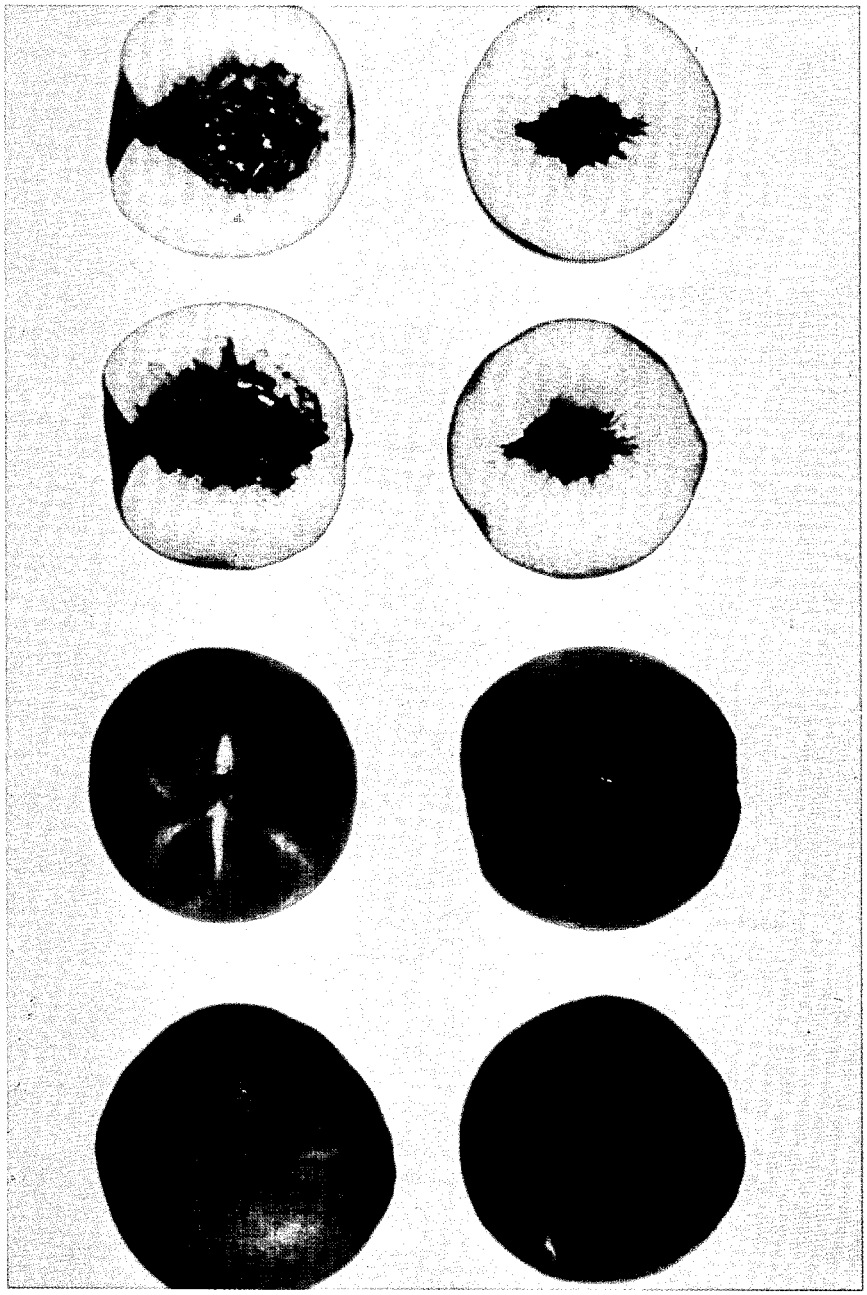

Plant Pat. 3,978

Patented Nov. 16, 1976

3,978
PEACH TREE

Claron O. Hesse, Kingsburg, Calif., assignor to The Regents of the University of California, Berkeley, Calif.

Filed Oct. 20, 1975, Ser. No. 624,151

Int. Cl.[2] A01H 5/03

U.S. Cl. Plt.—43 1 Claim

This invention relates to a new and distinct variety of peach tree which resulted from a complex cross, the pedigree of which is set forth below:

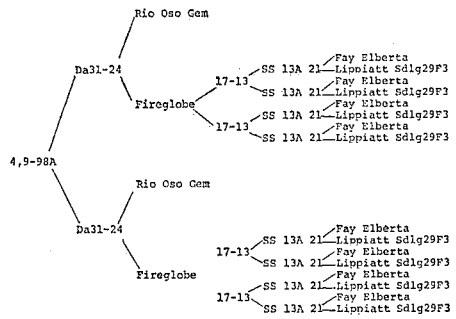

The last step self-pollination of Da31-24 was made in 1960.

The invention of Selection 4,9-98A was discovered in 1965 and subsequently asexually multiplied at the Kearney Horticultural Field Station, Fresno County, Calif. in 1968. Thereafter the new variety was placed in several authorized grower-cooperative trial plots and tested. These tests indicated the merit of this new peach tree and resulted in its selection as a promising variety.

FIG. 1 of the accompanying drawing illustrates peaches of the new variety which are typical in size, shape and color, some of which are shown in half sections, pitted and unpitted, and in which some of the variations in the size and shape of the fruit, its pit, and the color of the skin and flesh of this variety are indicated.

A distinguishing characteristic of this new tree is its early development of fruit having a high red blush which covers nearly the entire fruit surface by the time the fruit reaches shipping maturity. When tree ripe the fruit is fully blushed red.

It is further distinguished by the firmness of the flesh of the fruit, which flesh is a clear amber-yellow in color and without red until well past full ripeness. The fruit is of very good eating quality being sweet, rich, somewhat sprightly subacid, but essentially mild and having a moderate aroma.

The varietal characteristics of this new peach tree described below in detail were observed upon its discovery and subsequently through its test period. The color terminology as used herein is in accordance with Ridgway, Color Standards and Color Nomenclature (1912 Edition).

Tree:

*Size.*—Medium, vigor medium; upright-spreading with shape and density determined by pruning.

*Current seasons shoots.*—Applegreen, Plate XVII to Light Cress Green, Plate XXXI, tinged red where exposed.

*Trunk.*—Medium stout; medium rough; brown (Benzo Brown to Fuscous, Plate XLVI)

*Branches.*—Brown to reddish brown (Carob Brown, Plate XV to Mummy Brown, Plate XV); bark rough; peeling off in recurved platelets which adhere tightly; on younger branches growth cracks longitudinally striated showing light brown beneath (Dresden Brown, Plate XV).

*Lenticels.*—Moderately numerous, medium size, relatively inconspicuous with low, raised lips.

*Flower buds.*—Plump, pubescent.

Leaves: From midshoot leaves from shoots 18" to 20" long.

*Size.*—Medium; 16.7±0.99 cm. long x 3.8± cm. wide.

*Shape.*—Elliptic-lanceolate; base acuminate; apex long, acute-acuminate. Flat to somewhat recurved; apex more or less twisted.

*Blade.*—Thin; dark green above (Dark Dull Yellow Green, Plate XXXII), lighter below. Margin crenate, somewhat wavy. Midrib sparsely puberulent laterally, next to blade.

*Petiole.*—Short, 1.2±0.18 cm. long; moderately thick; channeled on ventral surface; Scheele's Green, Plate VI.

*Glands.*—Reniform, usually 4 or more on upper half of the petiole and on the base of the blade.

Flowers: 1–2 per node.

*Pedicel.*—Short, medium stout, glabrous, Greenish (Scheele's Green, Plate VI).

*Corolla.*—Color and surface red (Ox-Blood Red, Plate I) to greenish depending upon exposure; glabrous.

*Calyx lobes.*—Separate; almost conic in shape, apex generally pointed. 4 mm. at base by 4 mm. long. Lobes reflexed about 90°.

*Petals.*—Rather broad ovate to nearly round; 15 broad x 20 long to 18 broad x 18 mm. long. Margin more often slightly eroded and/or nicked or slightly cleft at apex, flattish to wavy; slight cupped; color clear pink (Rose Pink, Plate XII) becoming resaceous basally with age (Bordeaux, Plate XII). Claw 1–2 mm. medium long; medium stoutness. Showy phenotype.

*Stamens.*—42–44 in number. Anthers: Full, plump, bright red dorsally (Nopal Red, plate I); yellow ventrally (Light Cadmium, Plate IV) and in creases; pollen moderately plentiful, fertile. Filaments: 15 mm.±in length; equal to style. White at anthesis becoming rosaceous with age.

*Pistil.*—to 20 mm. in length, greenish. Ovary small, ovate, heavily pubescent; style glabrous except for basal few mm.; stigma capitate.

Fruit:

*Ripe.*—August 13 in 1973.

*Crop.*—Full for tree.

*Size.*—Medium to large; average weight of fruit 210.5 ±24.32 gms.

*Shape.*—Length 77.2±4.54 mm. x cheek diameter 77.4±2.78 mm. x suture diameter 77.5±2.30 mm. Broad elliptic, slightly truncate. Fairly regular and uniform; one ½ often slightly larger, or symmetrical with a somewhat protruding suture lip; apex depressed, or with a short, fleshy tip. Base may slope slightly toward the ventral suture. Ventral aspect: Broad elliptic to broad ovate; truncate at base, rounded or truncate at apex; ½'s nearly equal to 1 noticeably larger. Axial aspect: Nearly round; the dorsal side somewhat thinner than the ventral side.

*Base.*—Somewhat variable; rather small, flattened; at right angles to the fruit axis, or sloping slightly toward the ventral edge; broad oval in outline. Medium shallow depth, flaring-conic.

*Shoulders.*—Rounded or flat-rounded to the basal cavity; nearly regular and smooth, or slightly but grossly irregular. Not at all depressed dorsally or ventrally, or broadly barely grooved dorsally. Occasionally lightly creased ventrally.

*Suture.*—Usually a line mediumly, to lightly, shallowly and narrowly grooved medianly; more or less deeper apically, barely or not at all depressed basally. The whole suture edge smooth, or more commonly somewhat protruding; one-half often somewhat larger and forming a lip.

*Apex.*—Rounded, somewhat variable. Rather deeply creased apically, the crease running somewhat past the stylar scar, to rounded and not at all depressed with the apical point occasionally a low, fleshy tip. The stylar scar a small dot, sometimes raised on a low fleshy tip.

*Color.*—Ground color a rich amber (golden) yellow (Light Cadmium, Plate IV). Blush: Full colored except for stem marks at base. Semi to full deep red (Nopal Red to Ox-Blood Red, Plate I). Mostly washed with only obscure, fine blotching or streaking on the less highly colored areas. Bright, good, attractive.

*Pubescence.*—Short, fine, light.

*Flesh color.*—Medium yellow (firm ripe) to amber (golden yellow) (Empire Yellow to Light Cadmium, Plate IV) when soft ripe. Clear, bright, attractive. No red except for occasional short, radiating lines of red near cavity.

*Cavity color.*—Medium red (Carmine, Plate I) and whitish, with more or less callous formation.

*Adhesion.*—Freestone.

*Flesh.*—Medium thick, firm-melting; moderately fine.

*Flavor.*—Sweet, rich, moderate aroma; somewhat sprightly subacid, but essentially mild. Eating quality very good.

*Stone.*—Medium size; somewhat long elliptic to slightly obovate; moderately plump. Usually symmetrically in cheek view, or the dorsal edge slightly longer. Ventral edge rounded, the suture rather eroded, the wings close, rounded, occasionally interrupted or eroded; the lateral grooves close, deep, channeled, from base to apex. The dorsal edge protruding, rather narrow; moderately deeply channeled, the sides usually more or less interrupted; rounded (not sharp). The base slightly necked, of medium breadth; scar medium small, oval; the whole usually sloping somewhat toward the ventral edge. The apex usually a sharp, acuminate tip, occasionally blunt, lateral surfaces pitted and grooved; the pits mostly basal and rather shallow. The grooves of medium depth and width rounded. Color dark brown (Mahogany Red, Plate II), stained reddish basally only.

*Seed.*—Ovate; moderately plump; testas brown (Sanford's Brown, Plate II).

I claim:

1. The new and distinct variety of peach tree herein described and illustrated, and identified by the characteristics enumerated above.

No references cited.

ROBERT E. BAGWILL, Primary Examiner